(12) United States Patent
Liu et al.

(10) Patent No.: US 9,220,466 B2
(45) Date of Patent: Dec. 29, 2015

(54) SYSTEM AND METHOD FOR IMPLEMENTING WARM-UP SCANNING IN CT DEVICE

(71) Applicant: Shenyang Neusoft Medical Systems Co., Ltd., Shenyang (CN)

(72) Inventors: Jinjun Liu, Shenyang (CN); Qingxiang Shu, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 83 days.

(21) Appl. No.: 14/142,959

(22) Filed: Dec. 30, 2013

(65) Prior Publication Data

US 2015/0063530 A1    Mar. 5, 2015

(30) Foreign Application Priority Data

Aug. 28, 2013   (CN) .......................... 2013 1 0385176

(51) Int. Cl.
| | |
|---|---|
| *A61B 6/06* | (2006.01) |
| *G21K 1/04* | (2006.01) |
| *A61B 6/10* | (2006.01) |
| *A61B 6/03* | (2006.01) |
| *A61B 6/00* | (2006.01) |

(52) U.S. Cl.
CPC . *A61B 6/06* (2013.01); *A61B 6/032* (2013.01); *A61B 6/107* (2013.01); *A61B 6/54* (2013.01); *G21K 1/04* (2013.01)

(58) Field of Classification Search
CPC .............. A61B 6/00; A61B 6/03; A61B 6/06; A61B 6/10; A61B 6/107; A61B 6/54; A61B 6/545; G01N 23/00; G01N 23/02; G01N 23/04; G01N 23/045; G01N 23/06; G01N 23/08; G01N 23/083; A61N 5/10; A61N 5/103; A61N 5/1036; A61N 5/1042; A61N 5/1045; A61N 5/1048; A61N 5/1064; A61N 5/1065; A61N 5/1067; A61N 5/1092; A61N 5/1094; G21K 1/00; G21K 1/02; G21K 1/025; G21K 1/04; G21K 1/043; G21K 1/046
USPC ......... 378/4–20, 91, 101, 145, 147–153, 160, 378/204, 210, 901
See application file for complete search history.

(56) References Cited

U.S. PATENT DOCUMENTS

| | | |
|---|---|---|
| 6,320,929 B1 | 11/2001 | Von Der Haar |
| 2008/0317212 A1 | 12/2008 | Kuehn et al. |

FOREIGN PATENT DOCUMENTS

| | | |
|---|---|---|
| CN | 1593344 A | 3/2005 |
| CN | 1937959 A | 3/2007 |
| CN | 102790860 A | 11/2012 |

OTHER PUBLICATIONS

"Experience of Formulating CT Scanning Scheme for Replacing Bulb Tube Pre-heating", Chen Shengmin et al., Annual Academic Meeting of Radiology, 2005, p. 490-491, Jul. 2005.
"Simple discourse about correct operation of spiral CT machine", Chen Zhihui, Medical Equipment Information, vol. 18, No. 10, p. 42-44, 2003.
"Use and Maintenance of Imported CT Machine" Yang Huahuan et al., International Medical Health Newsletter, vol. 9, No. 8, p. 146-147, 2003.
The Second Office Action issued on Jun. 23, 2015, regarding the Chinese priority patent application (201310385176.9).

*Primary Examiner* — Anastasia Midkiff
(74) *Attorney, Agent, or Firm* — Kilpatrick Townsend & Stockton LLP

(57) ABSTRACT

A system and a method for implementing warm-up scanning in a CT device are provided. The method includes: closing a slot of a beam limiter before a warm-up scanning process is initiated; implementing the warm-up scanning process to a CT radiation source; and opening the slot of the beam limiter after the warm-up scanning process is finished. The target object may not need to move during the warm-up scanning process. Therefore, a second time scout image scanning is no longer necessary and extra ionization radiation may be avoided.

16 Claims, 4 Drawing Sheets

SYSTEM AND METHOD FOR IMPLEMENTING WARM-UP SCANNING IN CT DEVICE

CROSS REFERENCE TO RELATED APPLICATIONS

The present application claims priority to Chinese Patent Application No. 201310385176.9, filed on Aug. 28, 2013 and entitled "SYSTEM AND METHOD FOR IMPLEMENTING WARM-UP SCANNING IN CT DEVICE", the entire disclosure of which is incorporated herein by reference.

FIELD OF THE DISCLOSURE

The present disclosure generally relates to medical facilities, and more particularly, to a method and a system for implementing warm-up scanning in a CT device.

BACKGROUND OF THE DISCLOSURE

Nowadays, Computed Tomography (CT) has become one of the indispensable routine diagnostic techniques in the modern medical field. In a CT device, a radiation source is one of the most important consumable items. Rational use and maintenance of the radiation source are very important for extending the service life of the CT device and obtaining stable results from the CT device. It's necessary to pay attention to its heat capacity when the radiation source is in operation. If the CT device implements a clinical sequence scanning to a target object when the heat capacity is lower than a threshold value, the radiation source may be damaged.

In clinical practices, after a scout image scanning is implemented to the target object, it is required to determine whether the heat capacity is lower than the threshold value. If yes, a warm-up scanning process may be implemented to the CT radiation source to increase the heat capacity and thereby protect the radiation source. After the warm-up scanning, a clinical sequence scanning process may be implemented to the target object. If the current heat capacity is not lower than the threshold value, a clinical sequence scanning process may be implemented directly after the scout image scanning process.

However, during the warm-up scanning process, the target object may need to be unloaded from a patient table and moved out of the scanner room to avoid unnecessary ionization radiation. As a result, when the target object comes back to the patient table, his/her new position on the table may be different from the original position before he/she leaves, which means another scout image scanning may be necessary. Therefore, for implementing the warm-up scanning, not only inconvenience may be caused for moving the target object, which may be a serious problem when the target object has an injury or severe illness, but also the target object may suffer extra ionization radiation from another scout image scanning for relocation.

BRIEF SUMMARY OF THE DISCLOSURE

Embodiments of the present disclosure provide systems and methods for implementing warm-up scanning in a CT device. The target object may not need to move during the warm-up scanning process. Therefore, another scout image scanning is no longer necessary and extra ionization radiation may be avoided.

According to one embodiment, a method for implementing warm-up scanning in a CT device is provided. The method includes:
before a warm-up scanning process is initiated, closing a slot of a beam limiter;
implementing the warm-up scanning process to a CT radiation source; and
opening the slot of the beam limiter after the warm-up scanning process is finished.

Optionally, the method further includes: during the warm-up scanning process, initiating a gantry to rotate and controlling the gantry to rotate at a speed which is required in a clinical sequence scanning process to be implemented.

Optionally, the method further includes: controlling gates of the beam limiter to overlap.

Optionally, the slot closed before the warm-up scanning process is required to be open in a clinical sequence scanning process to be implemented.

Optionally, there are one or more beam limiter(s).

According to one embodiment, a system for implementing warm-up scanning in a CT device is provided, including:
first control device, adapted for closing a slot of a beam limiter before a warm-up scanning process is initiated;
a warm-up scanning device, adapted for implementing the warm-up scanning process to a CT radiation source; and
a second control device, adapted for opening the slot of the beam limiter after the warm-up scanning process is finished.

Optionally, the system further includes:
a rotation speed control unit, adapted for, during the warm-up scanning process, initiating a gantry to rotate and controlling the gantry to rotate at a speed which is required in a clinical sequence scanning process to be implemented.

Optionally, the first control device includes:
a first unit for closing the slot of the beam limiter before the warm-up scanning process is initiated; or
a second unit for controlling gates of the beam limiter o overlap before the warm-up scanning process is initiated.

Optionally, the second control device includes:
a third unit for opening the slot of the beam limiter after the warm-up scanning process is finished, where the slot is required to be open in a clinical sequence scanning process to be implemented.

Optionally, there are one or more beam limiter(s).

Compared with conventional techniques, embodiments of the present disclosure may have following advantages.

When the warm-up scanning process is implemented to the CT radiation source, slot(s) of the one or more beam limiters corresponding to the one or more CT radiation sources are kept closed to prevent X-ray from reaching the target object, such that the target object may not need to move during the warm-up scanning process. Therefore, another scout image scanning is no longer necessary and extra ionization radiation may be avoided.

Further, the quality of the scanning image may be improved and the time for initiating rotating the gantry can be saved.

BRIEF DESCRIPTION OF THE DRAWINGS

In order to clarify the disclosure and advantages thereof, accompanying drawings used in description of embodiments of the present disclosure will be described simply. Obviously, drawings described below are only illustrative and those skilled in the art can obtain other drawings based on these drawings without creative works.

DETAILED DESCRIPTION OF THE DISCLOSURE

Embodiments of the present disclosure provide methods and systems for implementing warm-up scanning in a CT device. In these embodiments, when a warm-up scanning process is implemented to one or more CT radiation sources, slot(s) of one or more beam limiters corresponding to the one or more CT radiation sources are kept closed to prevent X-rays from reaching the target object, such that the target object may not need to move during the warm-up scanning process. Therefore, one more scout image scanning is no longer necessary and extra ionization radiation may be avoided.

In order to clarify the above objects, features and advantages of the present disclosure, detail embodiments will be illustrated with reference to accompanying drawings.

Figure 1:
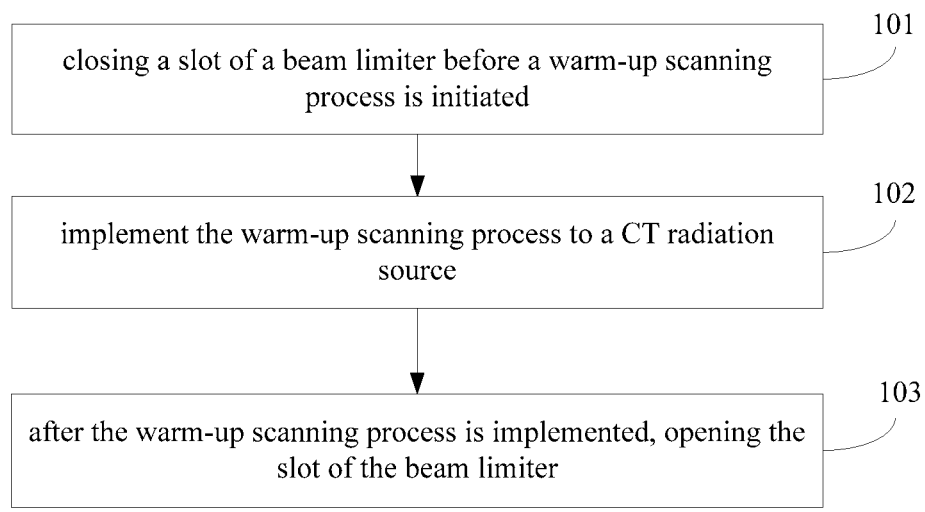
FIG. 1 schematically illustrates a flow chart of a method for implementing warm-up scanning in a CT device according to one embodiment of the present disclosure.

FIG. 1 schematically illustrates a flow chart of a method for implementing warm-up scanning in a CT device according to one embodiment of the present disclosure. Referring to FIG. 1, the method includes the steps of 101, 102 and 103.

In step 101, closing a slot of a beam limiter before a warm-up scanning process is initiated.

Normally, after a scout image scanning process, the current heat capacity of a CT radiation source may be sampled, so as to determine whether the current heat capacity is lower than a predetermined threshold value. If the current heat capacity is lower than the predetermined threshold value, a warm-up scanning process is needed to be implemented next. If the current heat capacity is not lower than the predetermined threshold value, there is no need for a warm-up scanning process and a clinical sequence scanning process can be implemented directly.

If a warm-up scanning process is determined to be implemented after the scout image scanning process, the slot of the beam limiter may be closed before the warm-up scanning process is implemented.

Specifically, the method may further include: controlling gates of the beam limiter to overlap.

In step 102, implement the warm-up scanning process to a CT radiation source.

Since the slot of the beam limiter is closed before the warm-up scanning process starts, the target object does not need to move during the warm-up scanning process, such that the target object may stay still.

In step 103, after the warm-up scanning process is implemented, opening the slot of the beam limiter.

Specifically, the slot is a slot required to be opened for implementing a clinical sequence scanning process.

Figure 2:
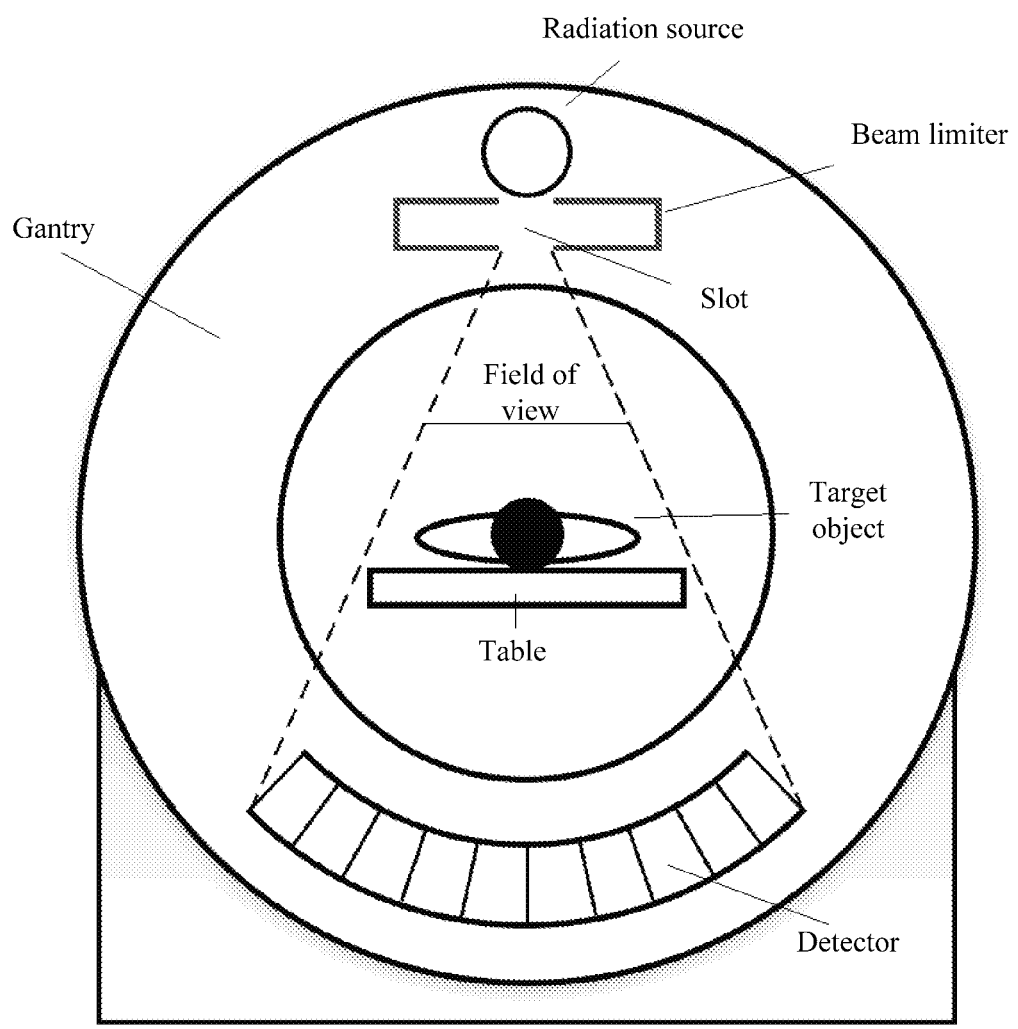
FIG. 2 schematically illustrates components of a CT device according to one embodiment of the present disclosure.

FIG. 2 schematically illustrates components of a CT device according to an embodiment of the present disclosure. As shown in FIG. 2, the CT device may include a gantry, on which a radiation source is provided. A beam limiter having a slot opened thereon is provided to control a field of view (FOW) of the CT device. In a chamber defined by the gantry, a patient table is equipped, such that the target object can be placed on the patient table. And a detector is provided under the patient table.

Before the warm-up scanning process is started, the slot of the beam limiter may be closed, and then the warm-up scanning process may be implemented to the CT radiation source. During the warm-up scanning process, since X-rays can't reach the target object, the target object can keep staying on the patient table and does not need to move.

It should be noted that, in some embodiments, the CT device may have one or more beam limiters and one or more CT radiation sources.

Compared with the conventional techniques, embodiments of the present disclosure may have following advantages.

When the warm-up scanning process is implemented to the one or more CT radiation sources, slot(s) of the one or more beam limiters corresponding to the one or more CT radiation sources are kept closed to prevent X-rays from reaching the target object, such that the target object does not need to move during the warm-up scanning process. Therefore, one more scout image scanning is no longer necessary and extra ionization radiation may be avoided.

To make sure that a clinical sequence scanning process can be implemented right after the warm-up scanning process is finished, in some embodiments, when the warm-up scanning process is implemented to the radiation source, the gantry may be initiated to rotate and controlled to rotate at a specific speed which is required in the clinical sequence scanning process.

Figure 3:
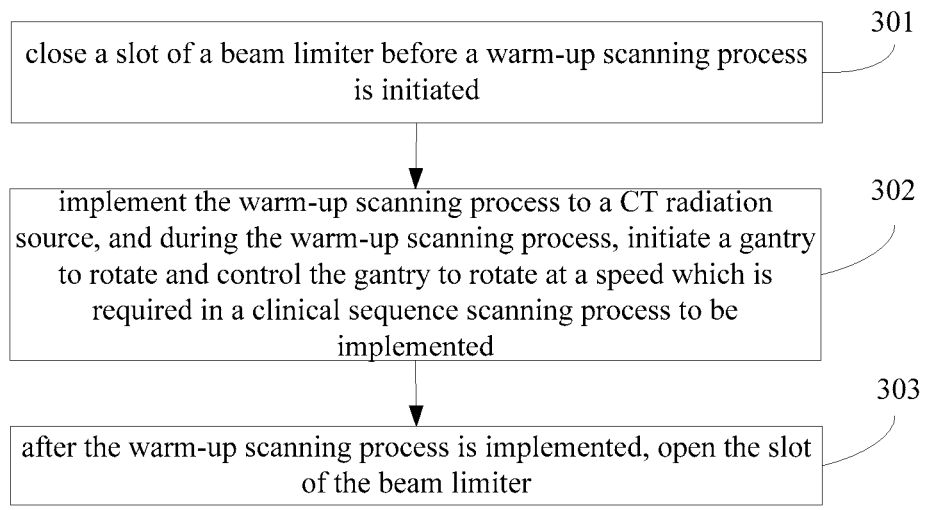
FIG. 3 schematically illustrates a flow chart of a method for implementing warm-up scanning in a CT device according to one embodiment of the present disclosure.

FIG. 3 schematically illustrates a flow chart of a method for implementing warm-up scanning in a CT device according to one embodiment. Referring to FIG. 3, the method includes steps 301, 302 and 303.

In step 301, close a slot of a beam limiter before a warm-up scanning process is initiated.

In step 302, implement the warm-up scanning process to a CT radiation source, and during the warm-up scanning process, initiate a gantry to rotate and control the gantry to rotate at a speed which is required in a clinical sequence scanning process to be implemented.

Suppose a rotation speed of the gantry required in the clinical sequence scanning process is A. When the warm-up scanning process is implemented, the gantry may be automatically initiated to rotate. Besides, the rotation speed is controlled to be A. As such, the inner temperature of the gantry chamber may have a good uniformity, which may be beneficial for improving the scanning image quality. Further, after the warm-up scanning process is finished, the slot of the beam limiter is opened. The clinical sequence scanning process may be implemented directly, because the current rotation speed of the gantry is A, which just meets the requirement of the clinical sequence scanning process. Therefore, the time for initiating rotating the gantry can be saved.

In step 303, after the warm-up scanning process is implemented, open the slot of the beam limiter.

Compared with conventional techniques, embodiments of the present disclosure may have following advantages.

When the warm-up scanning process is implemented to the one or more CT radiation sources, slot(s) of the one or more beam limiters corresponding to the one or more CT radiation sources are kept closed to prevent X-rays from reaching the target object, such that the target object does not need to move during the warm-up scanning process. Therefore, one more scout image scanning is no longer necessary and extra ionization radiation may be avoided.

Further, the scanning image quality may be improved and the time for initiating rotating the gantry can be saved.

Figure 4:
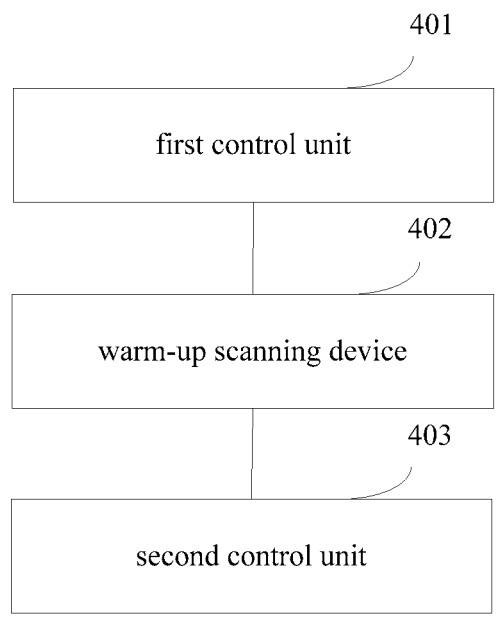
FIG. 4 schematically illustrates a block diagram of a system for implementing warm-up scanning in a CT device according to one embodiment of the present disclosure.

Corresponding to the methods for implementing warm-up scanning described above, systems for implementing warm-up scanning in a CT device are provided in embodiments of the present disclosure. FIG. 4 schematically illustrates a block diagram of a system for implementing warm-up scanning in a CT device according to one embodiment of the present disclosure. Referring to FIG. 4, the system includes: a first control device 401, a warm-up scanning device 402 and a second control device 403. Detail structures and interconnection relations of the components of the system will be illustrated hereinafter in conjunction with working principles.

The first control device 401 is adapted for closing a slot of a beam limiter before a warm-up scanning process is initiated.

The warm-up scanning device 402 is adapted for implementing a warm-up scanning process to a CT radiation source.

The second control device 403 is adapted for opening the slot of the beam limiter after the warm-up scanning process is finished.

Figure 5:
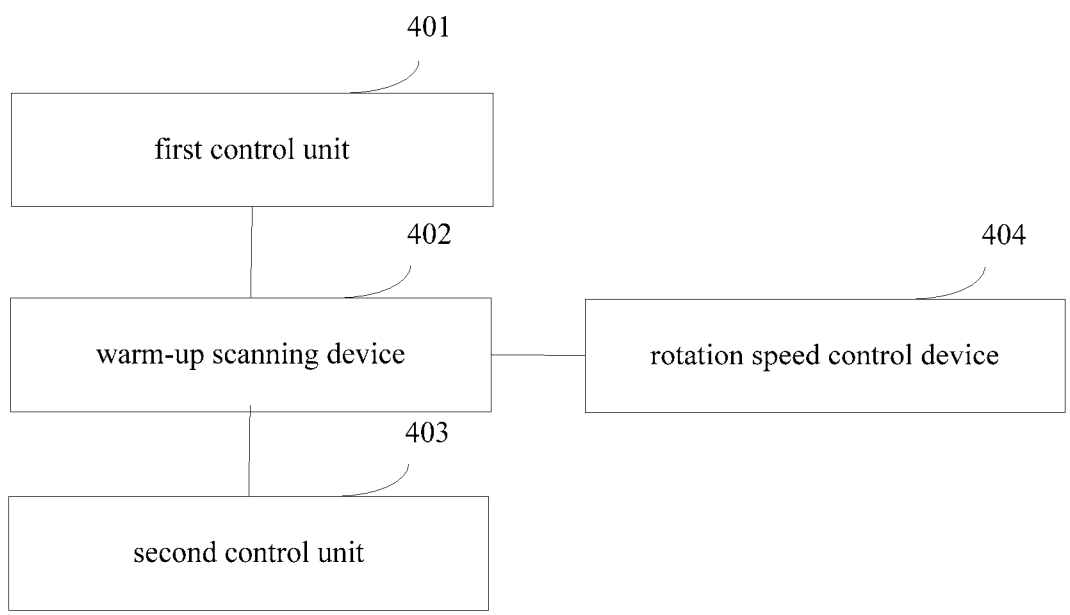
FIG. 5 schematically illustrates a block diagram of a system for implementing warm-up scanning in a CT device according to one embodiment of the present disclosure.

In some embodiments, as shown in FIG. 5 which schematically illustrates a block diagram of a system for implementing warm-up scanning in a CT device according to another embodiment, the system may further include a rotation speed control device 404. The rotation speed control device 404 is adapted for initiating a gantry to rotate and controlling the gantry to rotate to a speed which is required in a clinical sequence scanning process.

In some embodiments, the first control device 401 may include:
 a first unit for closing the slot of the beam limiter before the warm-up scanning process is implemented; or
 a second unit for controlling gates of the beam limiter to overlap before the warm-up scanning process is implemented.

In some embodiments, the second control device 403 may include:
 a third unit for opening the slot of the beam limiter after the warm-up scanning process is finished, where the slot is required to be open in a clinical sequence scanning process to be implemented.

In some embodiments, the system may include one or more beam limiters and one or more CT radiation sources.

Compared with conventional techniques, embodiments of the present disclosure may have following advantages.

When the warm-up scanning process is implemented to the one or more CT radiation sources, slot(s) of the one or more beam limiters corresponding to the one or more CT radiation sources are kept closed to prevent X-rays from reaching the target object, such that the target object does not need to move during the warm-up scanning process. Therefore, one more scout image scanning is no longer necessary and extra ionization radiation may be avoided.

Further, the scanning image quality may be improved and the time for initiating rotating the gantry can be saved.

Those skilled in the an could understand that, working procedures of systems, devices and units described above may be referring to methods provided in embodiments above, which are not illustrated in detail here for brief.

It should be noted that systems, devices and methods provided in embodiments of the present disclosure are merely examples, which can be implemented in alternative ways. For example, system embodiments described above are only illustrative. Divisions of devices and units in the system are only examples for dividing logic functions. Other divisions may be employed in practice. For example, several units or components may be combined or integrated in another system, or some features can be ignored or not performed. Besides, couplings, direct couplings or communication connections between units may be realized by some interfaces. Indirect couplings or communication connections between devices or between units may be electrical, mechanical or of other forms.

Units described as separated components may be separated physically or not. Components illustrated as units may be physical units or not, that is, they may be disposed in a same place or distributed in a plurality of network cells. Some or all of the units may be selected according to practical requirements to implement embodiments of the present disclosure.

Besides, units in embodiments of the present disclosure may be integrated in one processing unit or be separated physically, or at least two units thereof are integrated in one processing unit. The integrated units may be implemented by hardware or software.

It should be noted that, those skilled in the art may understand all or some of the processes in the methods described above can be realized by using computer programs to instruct corresponding hardware. The programs may be stored in a readable storage medium in a computer. When the programs are implemented, the processes in the methods in the above embodiments may be performed. The readable storage medium may be diskette, CD (Compact Disc), ROM (Read-Only Memory), RAM (Random Access Memory) or the like.

Systems and methods for implementing warm-up scanning in a CT device are described. Although the present disclosure has been disclosed above with reference to preferred embodiments thereof, it should be understood that the disclosure is presented by way of example only, and not limitation. Those skilled in the art can modify and vary the embodiments without departing from the spirit and scope of the present disclosure.

What is claimed is:

1. A method for implementing warm-up scanning in a CT device, comprising:
 closing a slot of a beam limiter before a warm-up scanning process is initiated;
 implementing the warm-up scanning process to a CT radiation source; and
 opening the slot of the beam limiter after the warm-up scanning process is finished.

2. The method according to claim 1, further comprising:
 during the warm-up scanning process, initiating a gantry to rotate and controlling the gantry to rotate at a speed which is required in a clinical sequence scanning process to be implemented.

3. The method according to claim 1, wherein the method further comprises: controlling gates of the beam limiter to overlap.

4. The method according to claim 1, wherein the slot opened after the warm-up scanning process is finished is a slot required to be open in a sequence scanning process to be implemented.

5. The method according to claim 1, wherein there are one or more than one beam limiter.

6. The method according to claim 2, wherein the method further comprises: controlling gates of the beam limiter to overlap.

7. The method according to claim 2, wherein the slot opened after the warm-up scanning process is finished is a slot required to be open in a clinical sequence scanning process to be implemented.

8. The method according to claim 2, wherein there are one or more than one beam limiter.

9. A system for implementing warm-up scanning in a CT device, comprising:
- a first control device, adapted for closing a slot of a beam limiter before a warm-up scanning process is initiated;
- a warm-up scanning device, adapted for implementing the warm-up scanning process to a CT radiation source; and
- a second control device, adapted for opening the slot of the beam limiter after the warm-up scanning process is finished.

10. The system according to claim 9, further comprising:
- a rotation speed control unit, adapted for, during the warm-up scanning process, initiating a gantry to rotate and controlling the gantry to rotate at a speed which is required in a clinical sequence scanning process to be implemented.

11. The system according to claim 9, wherein the first control device comprises:
- a first unit for closing the slot of the beam limiter before the warm-up scanning process is initiated; or
- a second unit for controlling gates of the beam limiter to overlap before the warm-up scanning process is initiated.

12. The system according to claim 11, wherein the second control device comprises:
- a third unit for opening the slot of the beam limiter after the warm-up scanning process is finished, where the slot is required to be open in a clinical sequence scanning process to be implemented.

13. The system according to claim 9, wherein there are one or more than one beam limiter.

14. The system according to claim 10, wherein the first control device comprises:
- a first unit for closing the slot of the beam limiter before the warm-up scanning process is initiated; or
- a second unit for controlling gates of the beam limiter to overlap before the warm-up scanning process is initiated.

15. The system according to claim 14, wherein the second control device comprises:
- a third unit for opening the slot of the beam limiter after the warm-up scanning process is finished, where the slot is required to be open in a clinical sequence scanning process to be implemented.

16. The system according to claim 10, wherein there are one or more than one beam limiter.

* * * * *